US006274141B1

(12) United States Patent
Monte

(10) Patent No.: US 6,274,141 B1
(45) Date of Patent: Aug. 14, 2001

(54) ENZYMATIC DIETARY TREATMENT FOR HYDROLYZING BSA

(75) Inventor: Woodrow C. Monte, Tempe, AZ (US)

(73) Assignee: Doyle W. Boatwright, Phoenix, AZ (US)

(*) Notice: Subject to any disclaimer, the term of this patent is extended or adjusted under 35 U.S.C. 154(b) by 0 days.

(21) Appl. No.: 08/395,867

(22) Filed: Feb. 28, 1995

(51) Int. Cl.[7] .................................................. A61K 38/48
(52) U.S. Cl. ................................. 424/94.64; 424/94.65; 426/530; 426/590; 426/656; 426/801
(58) Field of Search ................................. 426/530, 590, 426/656, 801; 424/94.64, 94.65

(56) References Cited

U.S. PATENT DOCUMENTS

| | | | | |
|---|---|---|---|---|
| 4,216,236 | * | 8/1980 | Müeller et al. | 426/72 |
| 4,294,856 | * | 10/1981 | Knumak et al. | 426/7 |
| 4,977,137 | * | 12/1990 | Nichols et al. | 514/6 |
| 4,981,704 | * | 1/1991 | Thibault | 426/41 |
| 5,039,532 | * | 8/1991 | Jost et al. | 426/41 |
| 5,135,869 | * | 8/1992 | Kaneko et al. | 4/268 |
| 5,356,637 | * | 10/1994 | Loosen et al. | 426/7 |
| 5,405,637 | * | 4/1995 | Martinez et al. | 426/850 |

OTHER PUBLICATIONS

Karjalainen, J. et al, "The New England J. of Medicine," vol. 327, #5, Jul. 1992, p. 302–307.*

Rennie, J., "Scientific American," vol. 267, #4, Oct. 1992, p. 24, 25.*

Baxter, A.G. et al., "Nature," vol. 359, Sep. 1992, p. 194–195.*

Shead, N.F., "Nutrition Reviews," vol. 51, #3 Mar. 1993, p. 79–81.*

Robinson, B.N., et al., "Diabetolegia," vol. 36, #4, Apr. 1993, p. 364–368.*

Chideckel, E.W. et al., "The New England J. of Med.," vol. 327, #22, Nov. 1992, p. 1602, 1603.*

Martin, J.M. et al., "Ann. Med.," vol. 23, #4, Oct. 1991, p. 447–452.*

Nosch, N.M. . "Clinical Biochem." vol. 26, Aug. 1993, p. 307–308.*

* cited by examiner

*Primary Examiner*—Jean C. Witz
(74) *Attorney, Agent, or Firm*—Tod R. Nissle, P.C.

(57) ABSTRACT

A method and apparatus enable the immune system of an infant to distinguish between ABBOS protein sections and p69 protein sections and reduces the risk that an infant will develop diabetes. The method cleaves protein-to-protein bonds in bovine serum albumin to reduce the similarity between the bovine serum albumin and pancreatic beta cells to minimize the likelihood that an infant will develop bovine serum albumin antibodies which will attack and kill the pancreatic beta cells.

14 Claims, No Drawings

ENZYMATIC DIETARY TREATMENT FOR HYDROLYZING BSA

This is a continuation of application Ser. No. 08/123,794, filed Sep. 20, 1993 now abandoned.

This invention pertains to a method and apparatus for enabling the immune system of an infant to distinguish between the ABBOS amino acid section of bovine serum albumin and the p69 amino acid section of insulin producing betacells.

In another respect the invention pertains to a method and dietary composition for reducing the risk that an infant will develop diabetes.

In a further respect, the invention relates to a method and apparatus for cleaving protein-to-protein bonds in bovine serum albumin to reduce the similarity between the bovine serum albumin and pancreatic beta cells to minimize the likelihood that an infant will develop bovine serum albumin antibodies which will attack and kill the pancreatic beta cells.

In a still another respect, the invention relates to a method and formulation for hydrolyzing protein-to-protein bonds in bovine serum albumin in a nutritional formulation which is administered to infants until "gut closure" occurs.

Bovine serum albumin (BSA) is one of the proteins contained in cow's milk. BSA includes a short, seventeen amino-acid section called ABBOS. Digestive enzymes in the small intestine of an adult break down ABBOS, and other portions of the BSA molecule, into amino acids or into chains of two or three amino acids. In contrast, the intestines of infants have fewer enzymes and typically allow large protein chains like BSA to pass directly into the bloodstream. When infants are from three to twelve months of age, "gut closure" occurs. When gut closure occurs, the infant develops additional enzymes which break down protein enzymes and prevent the passage of large protein chains directly into the bloodstream.

Anti-BSA antibodies exist in the very great majority, if not all, of children who drink cow's milk. Each anti-BSA antibody reacts to a particular section of the BSA molecule. Some of the anti-BSA antibodies react specifically to a short, 17 amino-acid section of the BSA molecule. This section is called ABBOS. Anti-BSA antibodies which react to the ABBOS section are also called anti-ABBOS antibodies. Consequently, an anti-ABBOS antibody is, by definition, an anti-BSA antibody. And, if an antiABBOS antibody is present, there likely are other anti-BSA antibodies present which are not anti-ABBOS antibodies.

Before gut closure occurs in an infant, the infant can develop antibodies which react to the ABBOS amino acid section of the BSA. The production of such ABBOS antibodies by an infant can be a problem because ABBOS is similar to a p69 amino acid section of insulin-producing beta cells. Beta cells are produced by the pancreas. The similarity between the ABBOS amino acid section and the p69 amino acid section causes antibodies to attack and destroy the beta cells, resulting in diabetes. Children with diabetes have been shown to have higher levels of antibodies against BSA. Further, apparently only children who are prone to develop diabetes are able to make anti-ABBOS antibodies, which are unusually rare in the population at large. Children with diabetes therefore appear to have immune systems which better identify ABBOS and produce antibodies which attack ABBOS.

It is believed that the p69 amino acid section of the insulin-producing beta cells appears only during times of stress, such as a viral infection. Further, it is also believed that more than one viral infection is required for the ABBOS antibodies to kill a sufficient number of beta cells to cause diabetes.

The entire problem of ABBOS antibodies attacking an infant's beta cells can be avoided if the immune system of the baby "sees" the p69 amino acid before it sees ABBOS and before it develops antibodies to ABBOS. Immediately after birth, the immune system of an infant has a general idea of which cells are part of the body, and are not be attacked, and which cells are foreign, and should be attacked. But the infant's immune system has to learn to identify specific foreign cells "on the fly". Accordingly, if the immune system of the infant views the p69 protein on a insulin-producing beta cell before it views ABBOS, then the immune system learns that the p69 protein is part of the infant's "in-house" processing system, and, the immune system will not subsequently attack the p69 protein. The production by the infant's beta cells of the p69 protein prior to the introduction of ABBOS into the infant's system cannot, of course, be guaranteed, which is why it is possible for ABBOS antibodies to be developed which subsequently attack p69 protein which it later first appears on the infant's beta cells.

BSA is found in cow's milk, in milk-like infant formulas based on non-fat cow milk (e.g., GERBER, SIMILAC, and CARNATION FOLLOW-UP infant formulas, and in whey predominant formulations (e.g., ENFIMIL, SMA infant formulas. As used herein, the term "milk formula" indicates cow's milk, a mother's breast milk, and milk-like infant formulas which contain BSA. The term "milk formula" also includes any other infant formula which is shown to include a peptide which can, in at least some infants, produce an antibody which attacks an amino acid section of insulin-producing beta cells. Further, it is important that manufactured milk formulations for infants have the proper proportions of protein, carbohydrates, and other nutritional components so that an infant's health is not adversely affected by ingesting the milk formulation. The components of nutritionally balanced manufactured infant milk formulations such as SIMILAC (Trademark), ENFAMIL (Trademark), and ISOMIL (Trademark) are well known in the art and will not be recited here.

The development by the infant's body of an antibody which attacks both a first protein and a second protein similar to the first protein is termed molecular mimicry. The development of a vaccine for smallpox exploited a case of molecular mimicry. When, in the late 18th century, smallpox was killing many people, another disease, cowpox, was common. Cowpox infected dairy cows and milkmaids. A cow infected with cowpox formed blisters on its udder. When their hands broke the blisters, milkmaids were infected with cowpox. The disease, however, was normally a mild one, and the milkmaids would fully recover. People who had cowpox would not get smallpox. As a result, in 1976 the English doctor Edward Jenner intentionally infected a boy with cowpox and then exposed the boy to smallpox. The boy did not contract smallpox. The development by the body of antibodies to cowpox is beneficial because these bodies then attack and destroy smallpox. The development by an infant's body of ABBOS antibodies is not, however, beneficial because the antibodies may attack and destroy insulin-producing beta cells.

Diabetes is one of the leading causes of death in the United States. Approximately 11 million Americans have diabetes, and about half of them do not know they are diabetic. Accordingly, it would be highly desirable to produce a method and apparatus for reducing the likelihood that an infant will, on ingesting a milk formula or other food product, develop antibodies which can attack insulin producing beta cells or other desirable living cells which the body produces and utilizes during its normal metabolic and physiological processes.

Therefore, it is a principal object of the invention to provide a method and apparatus for preventing the production by the immune system of antibodies harmful to desirable living cells in the body of an animal.

A further object of the invention is to provide a method and apparatus for altering the ABBOS on BSA in a milk formula to reduce the risk that ABBOS antibodies produced by an infant will attack insulin producing beta cells.

Another object of the invention is to provide a method and apparatus for altering protein-to-protein bonds of polypeptides in bovine serum albumin.

Briefly, I have discovered an article of manufacture for use in altering the appearance to the immune system of an infant of protein sections of bovine serum albumin. The article of manufacture includes a sealed container, and a nutritionally balanced milk formulation in the container. The milk formulation includes bovine serum albumin and includes an active protease enzyme in a concentration of 0.025 to 1000 milligrams of the enzyme per liter of the milk formulation. The protease enzyme acts in the container to cleave protein-to-protein bonds in at least some of the amino acid sections of the bovine serum albumin to alter the structure of the amino acid sections.

In another embodiment of the invention, I have discovered a dietary enzymatic process for enabling the immune system of an infant to distinguish between the ABBOS amino acid section of bovine serum albumin and the p69 amino acid section of insulin-producing beta cells. The process includes the step of preparing an infant milk formula. The infant milk formula is prepared by sterilizing a milk formulation and by adding a sterilized protease enzyme to the milk formulation in a concentration of 0.025 to 1000 milligrams of said enzyme per liter of the milk formulation. The milk formula is packaged in a sealed container. The protease enzyme acts while the milk formula is in the container to cleave peptide bonds of the bovine serum albumin to alter the ABBOS amino acid section of the bovine serum albumin to make the ABBOS amino acid section less similar to the p69 amino acid section of insulin-producing beta cells. The infant is fed by opening the container and administering the infant milk formula to the digestive tract of the infant such that the infant's immune system is exposed to the altered ABBOS amino acid section of the bovine serum albumin. If desired, the infant is fed the infant milk formula until the infant's insulin producing beta cells produce p69 protein or until gut closure occurs in the infant and the infant develops enzymes which break down protein enzymes and prevent the passage of large protein chains directly into the bloodstream of the infant.

The protease enzyme added to the milk formula is selected from, but not necessarily limited to, the group including papain, chymotrypsin, elastase, papain/chymo, and pepsinogen. A minor effective amount of 0.025 to 1000 milligrams, preferably 0.25 to 100 milligrams, of enzyme per liter of milk formula is utilized. Although the protease enzyme continues to cleave protein-to-protein bonds after the milk formula is placed in a sterile, sealed container, it is important that the protease enzyme not be present in a quantity sufficient to completely hydrolyze all of the bovine serum albumin polypeptide bonds to produce free amino acids prior to the sealed container being opened and prior to the milk formula in the container being fed to an infant. While typically up to about 10% to 15% by weight of the bovine serum albumin in the milk formula may be hydrolyzed to produce free amino acids, it is important that at least a portion of the ABBOS amino acid sections of the bovine serum albumin be only partially hydrolyzed so that the immune system of an infant will recognize, and possibly prepare antibodies for, such altered ABBOS amino acid sections.

Prior to adding the protease enzyme, the milk formula is typically, but not necessarily, sterilized by heating the milk to a temperature of 245 to 280 degrees Fahrenheit for four to twenty five seconds. Any other desirable process can be utilized to sterilize the milk formula. After the milk is cooled to room temperature, or after the milk is refrigerated, the protease enzyme is added. The protease enzyme is preferably, but not necessarily, sterilized. Sterilization of protease is accomplished by using well known filtration techniques or any other desirable procedure which sterilizes the protease without destroying the ability of the protease to hydrolyze protein-to-protein bonds.

After the protease enzyme is added to the milk formula, the formula is packaged. Preferably at least one to two weeks passes before the formula is ingested by an infant. While the formula can be ingested immediately after the protease is added to the formula, it is preferred to allow some time to pass to permit the protease enzyme to cleave polypeptide bonds to alter significantly the structure or "appearance" of the ABBOS amino acid section of the BSA molecules in the milk formula. Once the structure of the ABBOS section is altered, the immune system of the infant can distinguish the p69 protein from the ABBOS amino acid section. Consequently, any ABBOS antibodies which the infant produces is unlikely to attack the p69 protein and destroy insulin-producing beta cells.

A selected quantity of protease enzyme can be stored in a sealed packet for addition to cow's milk or other infant milk formulas purchased from a store. The protease enzyme is normally stored in a sealed packet along with a carrier. The carrier can be water or any other desired material which helps keep the protease enzyme active in the sealed packet. By way of example, and not limitation, a packet could include an amount of protease sufficient for a liter of milk or formula, e.g., each packet can include 0.025 to 1000 milligrams of protease enzyme, preferably 0.25 to 100 milligrams of enzyme. After a liter of fresh milk or another infant milk formula is purchased at a store, the contents of the packet are mixed into the milk. As soon as the contents of the packet are mixed into the milk, the protease begins to interact with BSA in the milk to cleave polypeptide bonds. The protease—milk composition is preferably permitted to set for a selected period of time before being administered to an infant. Allowing the protease—milk composition to set for a period of time enables the protease to cleave polypeptide bonds in the BSA before the protease—milk composition is ingested.

The following examples depict the presently preferred embodiments of the invention for the purpose of illustrating the practice thereof and not by way of limitation of the scope of the invention. In the examples, all proportions are by weight, unless otherwise noted.

EXAMPLE 1

A group of 71 children with an average age of eight years are diagnosed with type I diabetes and are tested for the presence of anti-BSA(bovine serum albumin) antibodies. A group of 39 children of the same age and 50 adults who do not have diabetes are tested for the presence of anti-BSA antibodies. The children with diabetes have about seven times more anti-BSA antibodies than the children and adults without diabetes. The children with diabetes have anti-ABBOS antibodies. The children without diabetes do not have anti-ABBOS antibodies.

EXAMPLE 2

One thousand liters of raw cow's milk is processed and sterilized. After the sterilized milk is cooled, 20 milligrams per liter of milk of sterilized papain is intermixed with the sterilized milk. The papain is sterilized by filtration or other processes which do not destroy the ability of the papain to hydrolyze protein-to-protein bonds in bovine serum albumin. The milk is packaged in sealed sterile containers and refrigerated. The milk contains bovine serum albumin (BSA).

EXAMPLE 3

One month after the milk is packaged in sealed containers in Example 2, one of the containers is opened and the milk is tested to determine whether protein-to-protein bonds of bovine serum albumin are cleaved by the papain enzyme and to determine whether bovine serum albumin is hydrolyzed to produce free amino acids. The test results indicate that protein-to-protein bonds of bovine serum albumin have been cleaved to alter the ABBOS amino acid section of the albumin; that all of the bovine serum albumin has not been hydrolyzed to produce free amino acids; and, that altered ABBOS amino acid sections are present in the milk.

EXAMPLE 4

Two months after the milk is packaged in sealed containers in Example 2, one of the containers is opened and the milk is tested to determine whether protein-to-protein bonds of bovine serum albumin are cleaved by the papain enzyme and to determine whether bovine serum albumin is hydrolyzed to produce free amino acids. The test results indicate that protein-to-protein bonds of bovine serum albumin have been cleaved to alter the ABBOS amino acid section of the albumin; that all of the bovine serum albumin has not been hydrolyzed to produce free amino acids; and, that altered ABBOS amino acid sections are present in the milk.

EXAMPLE 5

Three months after the milk is packaged in sealed containers in Example 2, one of the containers is opened and the milk is tested to determine whether protein-to-protein bonds of bovine serum albumin are cleaved by the papain enzyme and to determine whether bovine serum albumin is hydrolyzed to produce free amino acids. The test results indicate that protein-to-protein bonds of bovine serum albumin have been cleaved to alter the ABBOS amino acid section of the albumin; that all of the bovine serum albumin has not been hydrolyzed to produce free amino acids; and, that altered ABBOS amino acid sections are present in the milk.

EXAMPLE 6

One thousand liters of raw cow's milk is processed, sterilized, stored in sealed sterile containers, and refrigerated. The milk contains bovine serum albumin (BSA).

EXAMPLE 7

One week after the milk formulas of Examples 2 and 6 are prepared, a first group of 79 two month old healthy infants, hereafter called Group I, and a second group of 83 two month old healthy infants, hereafter called Group II, are tested for the presence of anti-BSA-antibodies and for the presence of antibodies against other specific ones of the cow's milk proteins in the milk formulas of Examples 2 and 6. No anti-BSA antibodies or antibodies against other specific ones of the cow's milk proteins are detected in the Group I or Group II infants. None of the infants in Group I and Group II has had a viral infection. Each infant in Group I and Group II has HLA genes which indicate a predisposition to developing diabetes. HLA genes are involved in the development of diabetes. In particular, HLA genes help regulate the immune response and determine the ability of an antigen-presenting white cell (APC) to bind and present a given antigen. After an APC cell engulfs a cell, it digests the cell and displays parts of the dead cell's structure on its surface. T cells sense and memorize this structure and pass this information along to B cells. The B cells manufacture antibodies which attack and are specific to that particular antigen. Tests for identifying HLA genes which indicate a predisposition to developing diabetes are well known in the art and will not be described herein. Prior to the antibody tests, the Group I and Group II infants are given only ISOMIL, a soybean based infant formula. After the anti-BSA-antibody test, the infants in Groups I and II are each fed orally in conventional fashion by permitting the infant to suckle the appropriate formulation through the nipple of a baby bottle as follows:

A. Each infant in Group I is fed exclusively for one month the milk formulation of Example 2 and after being fed the milk formulation of Example 2 for said one month period is again tested for the presence of anti-BSA antibodies and the presence of antibodies against other specific ones of the cow's milk proteins in the milk formulations of Examples 2 and 3. Anti-BSA-antibodies are not detected in any of the 79 infants of Group I. Methods for testing for the presence of anti-BSA antibodies and other antibodies are well known and will not be described herein.

B. Each infant in Group II is fed exclusively for one month the milk formulation of Example 6 and after being fed the milk formulation of Example 6 for said one month period is again tested for the presence of anti-BSA antibodies and the presence of antibodies against other specific ones of the cow's milk proteins in the milk formulations of Examples 2 and 6. Anti-BSA-antibodies are detected in each of the 83 infants of Group II. Anti-ABBOS antibodies are detected in 33 of the infants of Group II.

C. Each of the infants in Group I and Group II have about the same levels of antibodies against other specific ones of the cow's milk proteins in the milk formulations of Examples 2 and 6.

EXAMPLE 8

When the infants of Group I in Example 7 are eight years old, they are each tested for diabetes. In Example 7, the Group I infants were each fed the milk formulation of Example 2. None of the eight year old children in Group I has diabetes. Procedures for determining the presence of diabetes are well known and are not described herein.

EXAMPLE 9

When the infants of Group II in Example 7 are eight years old, they are each tested for diabetes. In Example 7, the Group II infants were fed the milk formulation of Example 6. Thirty-two of the thirty-three eight year old children who developed anti-ABBOS antibodies in Example 7 have diabetes. The remaining fifty children in Group II who developed anti-BSA antibodies, but not anti-ABBOS antibodies, in Example 7 do not have diabetes.

EXAMPLE 10

Example 7 is repeated, except that Group I is replaced by a third Group, hereafter called Group III, consisting of sixty-eight healthy two month old infants and Group II is replaced by a fourth group, hereafter called Group IV, consisting of sixty-three healthy two month old infants. Each infant in Groups III and IV has a HLA gene combination which protects the infants against diabetes. After the sixty-eight infants of Group III are fed the milk formula of Example 2 for one month and the sixty-three infants of Group IV are fed the milk formula of Example 6 for one month, the infants are tested for the presence of anti-BSA-antibodies. Anti-BSA-antibodies are detected in each of the sixty-eight infants of Group III and in each of the sixty-three infants of Group IV, but at lower levels than in the infants in Groups I and II in Example 4. None of the sixty-eight infants in Group III and the sixty-three infants in Group IV have anti-ABBOS antibodies.

EXAMPLE 11

When the infants of Group III and Group IV in Example 10 reach eight years of age, they are tested for diabetes. None of the sixty-eight children of Group III and the sixty-three children of Group IV has diabetes.

EXAMPLE 12

One thousand liters of SIMILAC infant milk formula (based on non-fat cow milk) is prepared. Ten milligrams per liter of milk of sterilized chymotrypsin is intermixed with the SIMILAC formula and the formula is sealed in cans. The chymotrypsin is sterilized by filtration or other processes which do not destroy the ability of the chymotrypsin to hydrolyze protein-to-protein bonds in bovine serum albumin. The SIMILAC formula contains bovine serum albumin (BSA).

EXAMPLE 13

One thousand liters of SIMILAC infant milk formula (based on non-fat cow milk) is prepared and sealed in cans. The SIMILAC formula contains bovine serum albumin (BSA).

EXAMPLE 14

Examples 4 to 11 are repeated, except that in Example 4 the milk formula of Example 12 is used in place of the formula of Example 2 and the milk formula of Example 13 is used in place of the formula of Example 6. Similar results are obtained.

EXAMPLE 15

Examples 2 to 11 are repeated, except that in Example 2 fifty milligrams per liter of milk of the sterilized protease enzyme pepsinogen is utilized in place of the twenty milligrams per liter of milk of papain. The pepsinogen is sterilized by filtration or other processes which do not destroy the ability of the pepsinogen to hydrolyze protein-to-protein bonds in bovine serum albumin. Similar results are obtained.

EXAMPLE 16

Examples 2 to 11 are repeated, except that in Example 2 only two milligrams per liter of milk of the sterilized protease enzyme pepsinogen is utilized in place of the twenty milligrams per liter of milk of papain. The pepsinogen is sterilized by filtration or other processes which do not destroy the ability of the pepsinogen to hydrolyze protein-to-protein bonds in bovine serum albumin. Similar results are obtained.

EXAMPLE 17

Examples 2 to 11 are repeated, except that in Example 2 eighty milligrams per liter of milk of the protease enzyme papain is utilized in place of the twenty milligrams per liter of milk of sterilized papain. Similar results are obtained.

EXAMPLE 18

Examples 2 to 11 are repeated, except that in Example 2 two hundred milligrams per liter of milk of the sterilized protease enzyme chymotrypsin is utilized in place of the twenty milligrams per liter of milk of papain. The chymotrypsin is sterilized by filtration or other processes which do not destroy the ability of the chymotrypsin to hydrolyze protein-to-protein bonds in bovine serum albumin. Similar results are obtained.

EXAMPLE 19

Examples 2 to 11 are repeated, except that in Example 2 five hundred milligrams per liter of milk of the sterilized protease enzyme pepsinogen is utilized in place of the twenty milligrams per liter of milk of papain. The pepsinogen is sterilized by filtration or other processes which do not destroy the ability of the pepsinogen to hydrolyze protein-to-protein bonds in bovine serum albumin. Similar results are obtained.

EXAMPLE 20

Examples 2 to 11 are repeated, except that in Example 7 the Group I and II infants are selected and fed the milk formulas of Examples 2 and 6 one month (instead of one week) after the milk formulas are prepared and placed in sealed containers. Similar results are obtained.

EXAMPLE 21

Examples 2 to 11 are repeated, except that in Example 7 the Group I and II infants are selected and fed the milk formulas of Examples 2 and 6 two months (instead of one week) after the milk formulas are prepared and placed in sealed containers. Similar results are obtained.

In order to be most effective in preventing the occurrence of diabetes in an infant, it is preferred that all milk formulas given the infant following birth be prepared in accordance with the invention, and, that all milk formula's ingested by the infant's mother also be prepared in accordance with the invention so that the mother will not pass ABBOS to the infant through her breast milk.

The milk formula prepared in accordance with the invention can be administered to the digestive tract in any conventional manner, for example by having an infant drink the formula, or by directing the formula through a feeding tube into the stomach or intestinal tract. Feeding tubes can extend down through the esophagus, through a surgical incision into the stomach or intestine, etc.

It is possible that the in vivo or in vitro use of enzymes to partially hydrolyze and alter the appearance of proteins may prevent molecular mimicry for amino acid sections other than the p69 section and may be otherwise useful in the treatment of disease.

Having described my invention in such terms as to enable those skilled in the art to understand and practice it, and having identified the presently preferred embodiments thereof, I claim:

1. An article of manufacture for use in altering the appearance to the immune system of an infant of protein sections of bovine serum albumin, said article of manufacture comprising
   (a) a sealed container;
   (b) a nutritionally balanced milk formulation in said sealed container, said milk formulation including bovine serum albumin and including an active protease enzyme in a concentration of 0.025 to 100 milligrams of said enzyme per liter of said milk formulation, said protease enzyme in said container cleaving protein-to-protein bonds to alter the structure of said bovine serum albumin.

2. A dietary enzymatic process for enabling the immune system of an infant to distinguish between the ABBOS amino acid section of bovine serum albumin and the p69 amino acid section of insulin-producing beta cells, comprising the steps of
   (a) preparing an infant milk formula, said infant milk formula being prepared by
      (i) sterilizing a milk formulation including bovine serum albumin;
      (ii) adding a sterilized protease enzyme to said milk formulation in a concentration of 0.025 to 100 milligrams of said enzyme per liter of said milk formulation;
   (b) packaging said infant milk formula prepared in step (a) in a sealed container such that while said milk formula is in said container, said protease enzyme cleaves peptide bonds of said bovine serum albumin to alter the ABBOS amino acid section of the bovine serum albumin such that anti-ABBOS antibodies produced by an infant ingesting said infant milk formula will not attack the p69 amino acid section of insulin-producing beta cells in the infant; and,
   (c) feeding the infant by opening said container and administering said infant milk formula to the digestive tract of the infant such that the infant's immune system is exposed to the altered ABBOS amino acid section of the bovine serum albumin.

3. The process of claim 2 wherein step (c) is carried out until the infant's insulin producing beta cells produce p69 protein.

4. The process of claim 2 wherein step (c) is carried out until gut closure occurs in the infant.

5. The process of claim 2 wherein in step (c) the only milk formulation which is fed to the infant after birth is the milk formula of step (a).

6. A dietary enzymatic process for altering the appearance to the immune system of an infant of bovine serum albumin, comprising the steps of
   (a) preparing an infant milk formula, said infant milk formula being prepared by
      (i) providing a nutritionally balanced milk formulation including bone serum albumin,
      (ii) adding protease enzyme to said milk formulation in a concentration of 0.025 to 100 milligrams of said enzyme per liter of said milk formulation;
   (b) packaging said infant milk formula prepared in step (a) in a container, said protease enzyme cleaving peptide bonds of said bovine serum albumin while said infant milk formula is in said container; and,
   (c) feeding an infant by opening said container and administering said infant milk formula to the digestive tract of the infant such that the infant's immune system is exposed to the altered amino acid section of the bovine serum albumin.

7. The article of manufacture of claim 1 wherein said enzyme cleaves peptide bonds of said bovine serum albumin to alter the ABBOS amino acid section of said bovine serum albumin such that anti-ABBOS antibodies produced by an infant ingesting said infant milk formula will not attack pancreatic insulin-producing beta cells in the infant.

8. The article of manufacture of claim 1 wherein said enzyme only partially hydrolyzes said bovine serum albumin.

9. The article of manufacture of claim 7 wherein said enzyme only partially hydrolyzes said ABBOS amino acid section.

10. The process of claim 2 wherein in step (b) said enzyme only partially hydrolyzes said ABBOS amino acid section.

11. The process of claim 6 wherein in step (b) said enzyme only partially hydrolyzes said bovine serum albumin.

12. The process of claim 6 wherein in step (b) said enzyme cleaves peptide bonds of said bovine serum albumin to alter said ABBOS amino acid section of said bovine serum albumin.

13. The process of claim 12 wherein in step (b) said enzyme only partially hydrolyzes said ABBOS amino acid section.

14. The process of claim 13 wherein in step (b) said enzyme hydrolyzes said ABBOS amino acid section such that anti-ABBOS antibodies produced by an infant ingesting said infant milk formula will not attack pancreatic insulin-producing beta cells in the infant.

* * * * *